United States Patent [19]

Kuwazuru et al.

[11] Patent Number: 5,665,432
[45] Date of Patent: Sep. 9, 1997

[54] PROCESS FOR TREATING TIMBER

[75] Inventors: Yosei Kuwazuru; Shinji Yoshida, both of Osaka-fu; Akira Igarashi, Hyogo-ken, all of Japan

[73] Assignee: Takeda Chemical Industries, Ltd., Osaka, Japan

[21] Appl. No.: 701,054

[22] Filed: Aug. 21, 1996

Related U.S. Application Data

[63] Continuation of Ser. No. 412,151, Mar. 28, 1995, abandoned.

[30] Foreign Application Priority Data

Mar. 29, 1994 [JP] Japan ............................ 6-059107
Dec. 28, 1994 [JP] Japan ............................ 6-326548

[51] Int. Cl.$^6$ ........................................... B05D 3/00
[52] U.S. Cl. ..................... 427/325; 427/388.4; 427/393; 427/440; 427/393.3; 427/393.4; 252/380
[58] Field of Search .................. 427/291, 297, 427/325, 388.4, 393, 393.3, 393.4, 440; 106/15.05; 252/380, 607

[56] References Cited

U.S. PATENT DOCUMENTS

| | | | |
|---|---|---|---|
| 14,522 | 7/1856 | Peddle | 427/325 |
| 1,456,509 | 5/1923 | Mai | 427/325 |
| 2,054,399 | 9/1936 | White, Jr. et al. | 427/325 |
| 2,350,845 | 6/1944 | Vaughan | 427/325 |
| 4,071,637 | 1/1978 | Dittstch et al. | 427/325 |
| 4,364,976 | 12/1982 | Prokofievna et al. | 427/440 |
| 5,035,956 | 7/1991 | Sedun | 427/440 |
| 5,300,520 | 4/1994 | Igarashi et al. | 514/367 |

Primary Examiner—Shrive Beck
Assistant Examiner—Brian K. Talbot
Attorney, Agent, or Firm—Wenderoth, Lind & Ponack

[57] ABSTRACT

It is an object to provide a process for treating timber, comprising the first step of immersing a high moisture content timber in an organic solvent compatible with water so as to remove water in the timber and make the organic solvent penetrate into the timber, and the second step of immersing the timber in a solution comprising a wood preservative and a high boiling point organic solvent, the solution being compatible with the organic solvent, so as to make the high boiling point organic solvent and the wood preservative penetrate into the timber, wherein timber is treated in a short period of time without a step of drying a high moisture content timber, and at the same time, cracking by drying at the step of drying a high moisture content timber is inhibited.

12 Claims, No Drawings

PROCESS FOR TREATING TIMBER

This application is a continuation of now abandoned application, Ser. No. 08/412,151, filed Mar. 28, 1995.

BACKGROUND OF THE INVENTION

1. Field of the Invention

The present invention relates to a process for treating a high moisture content timber specifically sawn for building.

2. Description of the Prior Art

Timber just after being cut down has a high moisture content, so that, when it is left to stand for a long time, it is easily attacked by microorganisms such as discoloring fungi, and cracks are caused by unequal shrinkage. Therefore, there is a problem that, unless some measures are taken, it becomes impossible to use the timber within a short period of time, without resulting in a loss of resources.

Then, hitherto, treatment with a wood preservative has been carried out to preserve timber. As methods of the treatment, the pressure process and the dip process wherein timber is treated with a wood preservative after drying, or the diffusion process wherein a high moisture content timber is treated with a wood preservative, have been mainly carried out. The former pressure process and the dip process have problems of a high cost and long time required in the drying stage, because timber must be sufficiently dried before the treatment with a wood preservative, which needs to be carried out under enough control to cause no cracking during drying. On the other hand, in the latter diffusion process, drying before treatment is not necessary, but it is not desirable as an industrial process, because it takes a long time for the treatment due to the property of diffusion, which makes timber stay for a long time in a state of high moisture content, so that undesirable microorganisms would easily grow.

SUMMARY OF THE INVENTION

The present inventors have earnestly studied in order to solve the above problems of drying a high moisture content timber and the treatment time, and have completed the present invention by finding that it is possible to treat timber in a short period of time without a conventional drying treatment, by treating a high moisture content timber under water vaporization condition in an organic solvent compatible with water, and then treating the timber with a solution comprising a wood preservative and a high boiling point organic solvent, the solution being compatible with the organic solvent. That is, it is an object of the present invention to provide a process for treating timber wherein it is possible to impregnate a high moisture content timber with a solution containing a wood preservative and so on in a short period of time without conducting a step of drying a high moisture content timber, and at the same time, it is possible to inhibit cracking at the usual step of drying a high moisture content timber.

And it was also found that the same effects can be obtained by immersing a high moisture content timber into a substantially water-free organic solvent which is compatible with water, and then treating the timber under reduced pressure.

DETAILED DESCRIPTION OF THE INVENTION

The first process for treating timber according to the present invention comprises the first step of immersing a high moisture content timber in an organic solvent compatible with water, so as to allow the organic solvent to penetrate into the timber and substitute for water until its moisture content is lowered at least to the level where no cracking by drying occurs, and the second step of immersing the timber in a solution comprising a wood preservative and a high boiling point organic solvent, the solution being compatible with the organic solvent, so as to allow the wood preservative and the high boiling point organic solvent to penetrate into the timber (hereinafter, referred to as two-step treatment process).

The second process for treating timber according to the present invention is characterized by immersing a high moisture content timber into a substantially water-free organic solvent which is compatible with water, and then treating the timber under reduced pressure (hereinafter, referred to as one-step treatment process).

First, the two-step treatment process is described.

The first step of the above two-step treatment process is carried out by immersing a high moisture content timber in an organic solvent compatible with water.

The high moisture content timber has a moisture content above the fiber saturation point. Unseasoned wood holds both free water contained in the cells and bonding water existing in the cell membranes. When timber having a moisture content above the fiber saturation point is dried, free water starts evaporating first, and bonding water starts evaporating when almost all the free water finishes evaporating. The situation where all of free water evaporates away, while bonding water is not lost yet so that the cell membranes are saturated with water, is the fiber saturation point. The fiber saturation point of timber depends on the kind of trees, but the moisture content ranges around 25 to 35 percent by weight. The present invention can be applied as it is to a high moisture content timber, but in order to carry out the treatment more effectively, the timber can be incised in advance. The modes of the incising treatment are, for example, to form holes 10 mm deep, 1 mm wide and 15 mm long at a density of 3500–4800/m$^2$ on a Western hemlock, Japanese Cedar, Japanese cypress and so on, or to form the above-shaped holes at a density of 4800–9000/m$^2$ on a Douglas fir, silver fir, Oregon pine, Japanese larch and so on, respectively. The incising treatment can be carried out in the usual way. To make the treatment density higher is better for penetration into timber, but an excessive number of holes unpreferably causes a lowering of strength of timber. The Japanese Agricultural Standard provides that a loss of strength shall be 10% and less.

The organic solvent used at the first step is what is compatible with water (hereinafter, referred to as an organic solvent compatible with water), and any solvent can be used as far as it satisfies the above condition and does not prevent the treatment carried out at the second step. The examples are alcohols such as ethanol, 1-propanol, 2-propanol, 3-methyl-3-methoxybutanol, 3-methoxybutanol, ethylene glycol monomethyl ether, ethylene glycol monoethyl ether, ethylene glycol monobutyl ether, diethylene glycol monomethyl ether, diethylene glycol monoethyl ether, diethylene glycol monobutyl ether and polyethylene glycol monomethyl ether, polyhydric alcohols such as ethylene glycol, glycerol, propylene glycol, diethylene glycol, triethylene glycol, polyethylene glycol and 3-methylbutane-1,3-diol, ketones such as acetone, nitriles such as acetonitrile, or polypropylene glycol, 1,3-butanediol, 1,4-butanediol, 1,5-pentanediol, trimethylene glycol, triethylene glycol monomethyl ether, triethylene glycol monoethyl ether, triethylene glycol dimethyl ether, tetraethylene glycol, dipropylene glycol, diethylene glycol monoethyl ether acetate, diethylene glycol diacetate, etc. Especially pasteurization effect by alcohols can be expected.

In the immersion at the first step, all that is required is a state where the timber is immersed in the organic solvent compatible with water. Therefore, it can be achieved, for example, either by pouring the organic solvent compatible with water into a vessel, and then immersing the timber therein, or by putting the timber in a vessel, and then pouring the organic solvent compatible with water thereinto, resulting in the same state as the timber is immersed in the organic solvent compatible with water. Through the step, part of water in the timber is removed, while the organic solvent penetrates thereinto in its place. That is, the organic solvent substitutes water. The immersion can be carried out at ordinary temperature and pressure, but in order to shorten the treatment time, it is preferable to increase temperature, and also preferable to reduce pressure in a sealed vessel. It is more preferable that immersion is carried out under such conditions of both increased temperature and reduced pressure as to allow water to easily vaporize. The higher the temperature, the shorter the reduced pressure time is required and the higher the degree of pressure reduction, the higher the removal rate of water occurs.

The second step according to the present invention is carried out by immersing the timber obtained after the treatment of the first step in a solution comprising a wood preservative and a high boiling point organic solvent, the solution being compatible with the organic solvent.

The high boiling point organic solvent required at the second step is any solvent that has the minimum boiling point of 150° C., preferably 200° C., and do not prevent a wood preservative from penetrating into timber. As high boiling point organic solvents, aliphatic or aromatic petroleum solvents, or diester phthalates are exemplified. As the aliphatic petroleum solvents, Exxon naphtha No. 7, Isopar L, Isopar M, Exxsol D110, Exxsol D130 (produced by Exxon chemicals), Nisseki Isosol 400, Naphtesol M, Naphtesol H (produced by Nippon Petro chemicals) and so on are cited. As the aromatic petroleum solvents, Solvesso 200 (produced by Exxon chemicals), Nisseki Hisol SAS296, Nisseki Hisol SASLH, Alkene L (produced by Nippon Petro chemicals), and so on are cited. Here, the aliphatic petroleum solvents and the aromatic petroleum solvents are divided on the basis of aniline point or mixed aniline point, that is, solvents having an aniline point above 30 are aliphatic petroleum solvents and solvents having a mixed aniline point of 30 and less are aromatic petroleum solvents. The examples of diester phthalate are dibutyl phthalate, di-2-ethylhexyl phthalate, dimethyl phthalate, diethyl phthalate and so on.

As wood preservatives, wood fungicides, insecticides, insect repellents and so on are exemplified.

As fungicides, for example, organic iodine fungicides such as 3-bromo-2, 3-diiodo-2-propenyl ethyl carbonate, 3-iodo-2-propynyl butyl carbamate, 2,3,3-triiodoallyl alcohol and parachlorophenyl-3-iodopropargylformal, benzimidazole or benzothiazole fungicides such as 2-(4-thiazolyl) benzimidazole and 2-thiocyanomethylthiobenzothiazole, triazole fungicides such as 1-(2-(2',4'-dichlorophenyl)-1,3-dioxolane-2-2-yl-methyl)-1H-1,2,4-triazole, 1-(2-2',4-dichlorophenyl)-4-propyl-1,3-dioxolane-2-yl-methyl-1H-1, 2,4-triazole and α-(2-(4-chlorophenyl)ethyl) -α-(1,1-dimethylethyl)-1H-1,2,4-triazole-1-ethanol, and aromatic fungicides such as benzoic acid are exemplified.

As insecticides, for example, organic phosphorus insecticides such as phoxim, chloropyrifos, fenitrothion, pyridaphenthione, isofenphos, pyrethroid insecticides such as cyfluthrin, permethrin, tralomethrin, fenvalerate, ethofenprox and Hoe-498, nitroguanidine insecticides such as imidacloprid, and nitromethylene insecticides are exemplified.

As insect repellents, for example, dibutyl succinate and diethyl toluamide are exemplified.

The solution used at the second step is usually what is made by dissolving a wood preservative and a high boiling point organic solvent in an organic solvent. The organic solvent usually has a boiling point of 100° C. and over, preferably 150° C. and over, and it can be any solvents wherein a wood preservative can be dissolved and which are compatible with a high boiling point organic solvent. As such organic solvents, Exxon naphtha No. 5, Exxon naphtha No. 6, Exxon orderless solvent, Solvesso 100, Solvesso 150, Exxsol D400, Isopar G, Isopar H, Isopar L (produced by Exxon chemicals), Nisseki Hisol 100, Nisseki Isosol 300, Naphtesol L (produced by Nippon Petro chemicals), Pegasol AS-100, Pegasol 3040, Pegasol AN-45, Pegasol R-100, Pegasol R-150 (produced by Mobil oil Co., Ltd.) and so on are exemplified.

In the solution used at the second step, the content of a high boiling point organic solvent is usually 10 wt % and over, preferably 20 wt % and over. And the content of a wood preservative is usually 0.01–20 wt %, preferably 0.5–5 wt %. In addition, the solution may contain, for example, effect reinforcing agents (e.g. octachloropropyl ether), resins (e.g. resins such as alkyd resin, acrylic resin, chlorinated paraffin, fluororesin and silicone resin, which form continuous layers in timber and inhibit water penetration), or other additives usually used for wood treatment agents (e.g. stabilizers such as antioxidants and ultraviolet light absorption agents, dyes, pigments and surface active agents) as well as a wood preservative and a high boiling point organic solvent. Any agent can be contained as long as it does not prevent penetration into a high moisture content timber.

In the immersion at the second step, all that is required is a state where the timber is immersed in the solution. Therefore, it can be achieved, for example, either by pouring the solution into a vessel, and then immersing the timber therein, or by putting the timber in a vessel, and then pouring the solution thereinto, resulting in the same state as the timber is immersed in the solution. Through the step, the solution comprising the high boiling point organic solvent and the wood preservative penetrates in a place of the organic solvent in the timber. The immersion can be carried out at ordinary temperature and pressure, but in order to shorten the treatment time, it may be preferable to increase temperature, and also preferable to reduce or increase pressure in a sealed vessel.

The manner of conducting the treatment comprises putting a high moisture content log or sawn wood in a treatment vessel, filling the vessel with an organic solvent compatible with water for the first step and, making water vaporize under reduced pressure and preferably at raised temperature, and then raising pressure back to ordinary one, draining, filling the vessel with a solution for the second step and raising temperature under reduced pressure to make the solution for the second step penetrate. If necessary, another step of penetration under increased pressure may be added. Through this process, the treatment of timber is completed.

In order to improve the treatment efficiency, it is better for the high moisture content timber to be incised. There are fiber cutting model and compression model as incising blades and the compression model is better, in consideration of capacity of treatment solution.

Next, the one-step treatment process is described.

The subject timber of the treatment has a high moisture content above the fiber saturation point, like unseasoned wood just after cut down, to which the advantages of the present invention can be demonstrated. And in order to carry out the treatment more effectively, it is better for the timber to be incised in advance. The manner of the incising treatment the same as that of the two-step treatment process. Incising treatment itself can be carried out in the usual way.

In the one-step treatment process, by immersing the high moisture content timber in a substantially water-free organic solvent which is compatible with water, the solution is allowed to penetrate into the timber. The substantially water-free organic solvent compatible with water is an organic solvent on the market to which no water is positively added, and water originated from purity of the article on the market or moisture absorption in use is not concerned. As the kinds of the organic solvents compatible with water, such organic solvents as are used at the first step in the two-step treatment process are exemplified, and among them, the solvents having a high boiling point of 150° C. and over are especially preferable. As the examples of the high boiling point organic solvents compatible with water, polyethylene glycol, polyethylene glycol monomethyl ether, polypropylene glycol, 1,3-butanediol, 1,4-butanediol, 1,5-pentanediol, glycerol, trimethylene glycol, triethylene glycol monomethyl ether, triethylene glycol monoethyl ether, triethylene glycol dimethyl ether, triethylene glycol, tetraethylene glycol, dipropylene glycol, diethylene glycol monobutyl ether, diethylene glycol monoethyl ether acetate, diethylene glycol monoethyl ether, diethylene glycol diacetate and diethylene glycol are exemplified, but the solvents are not limited to these. In addition, the organic solvents can be used in the form of a mixture of two or more sorts. As for polyethylene glycol, its mean molecular weight is preferably 20000 and less, and more preferably 400–1000.

It is desirable to use the organic solvent compatible with water mixed with a high boiling point organic solvent uncompatible with water in such a range as the organic solvent compatible with water is not prevented from penetrating into the timber. As the examples of the high boiling point organic solvents uncompatible with water, aliphatic petroleum solvents such as Exxon naphtha No. 7, Isopar L, Isopar M, Exxsol D80, Exxsol D110, Exxsol D130 (produced by Exxon chemicals), Naphtesol M, Naphtesol H, Nisseki Isosol 400 (produced by Nippon Petro chemicals), and aromatic petroleum solvents such as Solvesso 200 (produced by Exxon chemicals), Nisseki Hisol SAS296, Nisseki Hisol SASLH and Alkene L (produced by Nippon Petro chemicals) and exemplified. Besides, ester phthalate such as dibutyl phthalate, di-2-ethylhexyl phthalate, dimethyl phthalate and diethyl phthalate are exemplified. Here, the aliphatic petroleum solvents and the aromatic petroleum solvents are divided in the same manner as that of the two-step treatment process.

In the immersion treatment, all that is required is a state where the timber is immersed in the solution containing the organic solvent compatible with water. Therefore, it can be achieved, for example, either by pouring the solution containing the organic solvent compatible with water into a vessel, and then immersing the timber therein, or by putting the timber in a vessel, and then pouring the solution containing the organic solvent compatible with water thereinto, resulting in the same state as the timber is immersed in the solution containing the organic solvent compatible with water. Through the step, part of water in the timber is removed, while the solution containing the organic solvent compatible with water penetrates thereinto in its place. That is, the organic solvent compatible with water substitutes for water in the timber. The immersion can be carried out at ordinary temperature and pressure, but in order to shorten the treatment time, it is preferable to increase temperature. And after immersing, it is preferable for the timber to be treated under reduced pressure in a sealed vessel.

In the organic solvent compatible with water, a wood preservative can be contained, and in this case, the used wood preservative is the same as that in the two-step treatment process. The content of the wood preservative is preferably 0.01–20 percent by weight. In order to be more stabilized, for example, the wood preservative can take the form of inclusion.

Besides, the organic solvent compatible with water may contain, for example, resins, stabilizers such as antioxidants and ultraviolet light absorption agents, dyes, pigments, surface active agents as well as the wood preservative in the same manner as that in the two-step treatment process, as long as they do not prevent penetration into a high moisture content timber and substitution for water. Moreover, aliphatic petroleum solvents or aromatic petroleum solvents can be added, as long as they do not prevent penetration and substitution for water.

The manner of conducting the one-step treatment process comprises putting a high moisture content log or sawn wood in a treatment vessel, filling the vessel with the solution containing the organic solvent compatible with water and making water evaporate under reduced pressure and preferably at raised temperature, while making the solution containing the organic solvent compatible with water penetrate, and then raising pressure back to ordinary one in the treatment vessel and draining. If necessary, another step of penetration under increased pressure may be added. The treatment of timber is completed through this process. In order to improve the treatment efficiency, it is preferable for a high moisture content log or sawn wood to be incised. There are fiber cutting model and compression model as incising blades and the compression model is better, in consideration of capacity of treatment solution.

In the one-step treatment process, it is preferable that the treatment time is as short as possible. That is, there is no need that all water inside timber is substituted by a solution containing an organic solvent compatible with water. Even substitution only in the surface layer of timber may have sufficient effect on anti-cracking from shrinkage and wood preservation.

DESCRIPTION OF PREFERRED EMBODIMENTS

1. Examples by Two-step Treatment Process

A. Wood Fungicide Treatment Test on High Moisture Content Timbers (1) The kind, size and moisture content of the used high moisture content timbers are as follows;

kind of tree: each sapwood of Western hemlock, Japanese cedar and Japanese cypress, size: the cut ends of 30×30 mm, which were sealed with epoxy resin, and the length of 120 mm, and moisture content: all test pieces of wood had a moisture content of 100% or more. (Here, moisture content is % ratio of the weight of contained water to the weight of whole dried wood. Hereinafter, moisture content is based on this standard.)

(2) Treatment Conditions (a) Number of Treated Wood Pieces

Three pieces of Western hemlock, Japanese cedar and Japanese cypress were treated. Here, other three pieces of the trees without going through the first-step treatment were prepared and only the second-step treatment was carried out thereon.

(b) Pretreatment (Incising Treatment)

Holes 5 mm long, 5 mm deep and 1 mm wide were formed on every surface at a density of 30/42 cm².

(c) Treatment Conditions at Every Step (i) Treatment conditions at the first step Treatment temperature: room temperature, treatment pressure: 100 mmHg, and treatment time: 2 hours (in the case of polyethylene glycol (PEG), treatment temperature: 80° C., treatment pressure: 100 mmHg, and treatment time: 2 hours)

(ii) Treatment conditions at the second step

Treatment temperature: 80° C., treatment pressure: 100 mmHg, and treatment time: 1 hour (d) Treatment Solutions (i) Organic solvents compatible with water used for treatment at the first step Ethanol, 1-propanole, acetonitrile, acetone, PEG200, PEG400 and PEG600

(ii) Organic solvents used for treatment at the second step

TABLE 1-1

Organic solvents used for treatment at the second step

| Solvent | Prescription number | | | | |
|---|---|---|---|---|---|
| | a wt % | b wt % | c wt % | d wt % | e wt % |
| dibutyl phthalate | 100 | 80 | 80 | 60 | — |
| aromatic petroleum solvent *1 | — | — | — | — | 100 |
| phoxim | — | 1 | — | 1 | — |
| cyfluthrin | — | — | 0.1 | — | — |
| propiconazole | — | 1 | 1 | — | — |
| IPBC *2 | — | — | — | 1 | — |
| alkyd resin *3 | — | — | 5 | 5 | — |
| aromatic solvent *4 | — | 18 | 13.9 | 33 | — |

TABLE 1-2

| Solvent | Prescription number | | | |
|---|---|---|---|---|
| | f wt % | g wt % | h wt % | i wt % |
| dibutyl phthalate | — | — | — | 40 |
| aromatic petroleum solvent *1 | 80 | 80 | 60 | 40 |
| phoxim | 1 | — | 1 | 1 |
| cyfluthrin | — | 0.1 | — | — |
| propiconazole | 1 | 1 | — | 1 |
| IPBC *2 | — | — | 1 | — |
| alkyd resin *3 | — | 5 | 5 | 5 |
| aromatic solvent *4 | 18 | 13.9 | 33 | 13 |

Note 1)
In order to measure penetration depth, zinc caprylate of 0.5 wt % was added to the organic solvent.
Note 2)
*1: an aromatic petroleum solvent having a minimum boiling point of 200° C. (phenylxylylethane)
*2: I — C = C-CH$_2$OCONHC$_4$H$_9$
*3: soybean oil modified alkyd resin (long oil type having a oil lenght of 63%)
*4: an aromatic solvent having a mixed aniline point of 16.0

(3) Treatment Results

After the treatment was completed, the wood pieces used in the test were cut off at intervals of 3 cm and the penetration depth of the cut ends were measured by visual observation.

Then, the wood pieces whose cut ends had a mean penetration depth of 3 mm or more, and less than 3 mm, were regarded as ○ and x, respectively. The solutions used at the first and second steps, and the results are shown in Table 2.

TABLE 2

| First-step treatment solution | Second-step treatment solution | Result |
|---|---|---|
| ethanol | a | o |
| ethanol | b | o |
| ethanol | c | o |
| ethanol | d | o |
| ethanol | e | o |
| ethanol | f | o |
| ethanol | g | o |
| ethanol | h | o |
| ethanol | i | o |
| 1-propanol | b | o |
| acetonitrile | b | o |
| acetone | b | o |
| PEG200 | b | o |
| PEG400 | b | o |
| PEG600 | b | o |
| uncompatible solvent with water | a | x |
| uncompatible solvent with water | e | x |

The same results as those in Table 2 were true of all 3 kinds of trees. From the above results, comparing with the wood pieces without going through the first-step treatment, it is found that the solution containing a wood preservative penetrated well into the timber in the process according to the example.

Next, another treatment was carried out with using the solution below-described in Table 3, under the same conditions except that holes of incising treatment were 5 mm deep and 1 mm wide, formed at a pitch of 5 mm vertically by 5 mm horizontally. The solutions used at the first and second steps, and the results are shown in Table 3.

TABLE 3

| First-step treatment solution | Second-step treatment solution | Result |
|---|---|---|
| ethanol | b | 10 mm and over |
| ethanol | e | 10 mm and over |
| PEG200 | b | 10 mm and over |
| uncompatible solvent with water | a | x |
| uncompatible solvent with water | e | x |

From the above results as shown in Table 3, it is found that the solutions containing a wood preservative penetrated deeper into the timber by the treatment carried out under the above conditions with water miscible solvent in the first-step.

B. Cracking Prevention Test of Timber (1) The kind, size and moisture content of the used high moisture content timbers are as follows;

kind of tree: Japanese Cedar and Japanese cypress, size: the cut ends of 90×90 mm and the length of 150 mm (including heartwood), and moisture content: all test blocks had a moisture content of 100% or more.

(2) Treatment Conditions (a) Number of Treated Wood Blocks

Three wood blocks having cut ends Japanese cedar and Japanese cypress were treated. Here, other three blocks of each tree having sealed cut ends remained going through the first-step.

(b) Treatment Conditions at Each Step (i) Aging conditions
temperature: room temperature (ii) Treatment conditions at the first step
Treatment temperature: 80° C., treatment pressure: 100 mmHg and treatment time: 1 hour (3) Treatment Solutions
Treatment solution at the first step: ethanol (4) Treatment Results As for the blocks which were treated at first-step, no cracking by drying was found after aging. Cracking by drying was found on the blocks without going through the first-step treatment.

2. Examples by One-step Treatment Process

A. Moisture Content Lowering Test on High Moisture Content Timbers (1) Kind and size of the used high moisture content timbers: the same as those in the above two-step treatment process, and moisture content in the initial stage: 250% and over in all of the test pieces.

(2) Treatment Conditions (a) Number of treated wood pieces: the same as that in the above two-step treatment process (b) Pretreatment (Incising Treatment)

Holes 5 mm deep, 1 mm wide and having a pitch of 5 mm vertical by 5 mm horizontal were formed at a density of 30/42 cm².

(c) Treatment conditions (temperature, pressure and time) are shown in Table 4.

TABLE 4

| Treatment condition number | Treatment temperature (°C.) | Treatment pressure (mmHg) | Treatment time (hour) |
| --- | --- | --- | --- |
| ① | 80 | 100 | 2 |
| ② | 80 | 100 | 1 |
| ③ | 80 | 10 | 2 |
| ④ | 80 | 10 | 1 |
| ⑤ | 80 | 100 | 4 |

(d) Treatment solutions (Here, non-aqueous Ceres blue of 0.1 percent by weight was added to the below solutions in order to measure penetration depth.)

I PEG400
II PEG600
III polyethylene glycol monomethyl ether (molecular weight of about 220)
IV polypropylene glycol (molecular weight of about 400)
V 1,3-butanediol
VI glycerol
VII trimethylene glycol
VIII triethylene glycol monomethyl ether
IX PEG400: 96 wt %, benezoic acid: 1 wt % and Solvesso 200 (produced by Nippon Petro chemicals): 3 wt %
X PEG400: 88 wt %, dibutyl phthalate: 10 wt %, Bassa: 1 wt % and IPBC: 1 wt %

XI dibutyl phthalate: 100 wt %

(3) Treatment Results

The pieces used in the test were cut off at intervals of 3 cm after the treatment was completed and the penetration depth of the cut ends were measured with a scale.

Then, the pieces whose cut ends had a mean penetration depth of 10 mm or more, 9–3 mm, and 2 mm or less, were graded as A, B, and C, respectively. The kinds of trees, solutions, treatment conditions and results (penetration depth) are shown in Table 5.

TABLE 5

| Kind of tree | Solution | Treatment condition number | Osmosis degree |
| --- | --- | --- | --- |
| Japanese Cedar | I | ① | A |
| Japanese Cedar | I | ② | B |
| Japanese Cedar | I | ③ | B |
| Japanese Cedar | I | ④ | B |
| Japanese Cedar | II | ① | A |
| Japanese Cedar | III | ① | B |
| Japanese Cedar | IV | ① | B |
| Japanese Cedar | V | ① | B |
| Japanese Cedar | VI | ① | B |
| Japanese Cedar | VII | ① | B |
| Japanese Cedar | VIII | ① | B |
| Japanese Cedar | IX | ① | B |
| Japanese Cedar | X | ① | B |
| Japanese Cedar | XI | ① | C (Comparative Example) |
| Japanese cypress | I | ① | B |
| Japanese cypress | II | ① | B |
| Japanese cypress | X | ① | B |
| Oregon pine | I | ① | B |
| Oregon pine | II | ① | B |
| Oregon pine | X | ① | B |

From the results as shown in Table 5, it is found that the solutions containing a high boiling point water miscible solvent penetrated well into the timber or water in wood pieces was effectively removed.

Next, as for four items from the top among the treated pieces shown in Table 5, each material balance was measured. The results are shown in Table 6.

TABLE 6

| Kind of tree | Solution | Treatment condition number | penetration depth | Moisture content before treatment (%) | Moisture content after treatment * (%) |
| --- | --- | --- | --- | --- | --- |
| Japanese Cedar | I | ① | A | 271 | 101 |
| Japanese Cedar | I | ② | B | 269 | 130 |
| Japanese Cedar | I | ③ | B | 277 | 35 |
| Japanese Cedar | I | ④ | B | 278 | 49 |
| Japanese Cedar | I | ⑤ | A | 270 | 36 |

*Moisture content after treatment includes the part into which no treatment solution penetrated.

From the results as shown in Table 6, it is found that the moisture contents after treatment were greatly lowered. Thus, moisture in the timber was driven away and quantity of moisture decreased through the treatment of the timber by the above method, so that drying effect of the treatment was proved.

B. Cracking Prevention Test of Timber (1) Kind, size and moisture content of the used high moisture content timbers: the same as those in the two-step treatment process (2) Treatment Conditions (a) Number of treated wood blocks: the same as that in the two-step treatment process (b) Treatment conditions (temperature, pressure and time)

Treatment temperature: 80° C., treatment pressure: 100 mmHg and treatment time: 2 hours (3) Treatment Solutions Solutions of sample numbers I, II, IX and X in Table 5

(4) Treatment Results

As for the blocks whose cut ends were sealed, no cracking by drying was found after the treatment. Cracking by drying was found on the untreated blocks, even if their cut ends were sealed.

What is claimed is:

1. A process for treating timber, consisting essentially of:
   providing a freshly sawn timber having a high moisture content above a fiber saturation point of the timber,
   immersing the high moisture content timber which has not been subjected to a drying treatment in a first liquid consisting essentially of a first organic solvent compatible with water, and then subsequently without drying,
   immersing the timber in a second liquid consisting essentially of a wood preservative and a second organic solvent which has a boiling point of not less than 150° C., the second liquid being compatible with the first organic solvent.

2. The process for treating timber according to claim 1, wherein the first organic solvent comprises an alcoholic solvent.

3. The process for treating timber according to claim 2, wherein the alcoholic solvent is a polyol.

4. The process for treating timber according to claim 1, wherein the second liquid contains the second organic solvent in an amount of at least 10 wt %.

5. The process for treating timber according to claim 1, wherein the second liquid contains the wood preservative in an amount of 0.01–20 wt %.

6. The process for treating timber according to claim 1, wherein the wood preservative comprises at least one of insecticides and fungicides.

7. The process for treating timber according to claim 1, wherein the first immersing step is carried out under conditions of temperature and pressure which accelerate vaporization of water from the timber.

8. The process for treating timber according to claim 1, wherein the second immersing step is carried out under conditions of temperature and pressure which accelerate vaporization of water from the timber.

9. The process for treating timber according to claim 1, wherein the high moisture content timber is incised.

10. A process for treating timber, consisting essentially of:
    providing a freshly sawn timber having a high moisture content above a fiber saturation point of the timber,
    immersing the high moisture content timber which has not been subjected to a drying treatment in a liquid consisting essentially of a substantially water-free organic solvent which is compatible with water, and then
    subjecting the timber to conditions of temperature and pressure which accelerate vaporization of water from the timber.

11. A process for treating timber according to claim 10, wherein a wood preservative is present in said liquid.

12. The process for treating timber according to claim 10, wherein the substantially water-free organic solvent has a boiling point of not less than 150° C.

* * * * *